(12) United States Patent
Underwood et al.

(10) Patent No.: US 8,650,935 B2
(45) Date of Patent: Feb. 18, 2014

(54) METHOD OF TOC MONITORING

(75) Inventors: Lee Underwood, Bucks (GB); Paul Whitehead, Henley (GB)

(73) Assignee: VWS (UK) Limited, Marlow, Bucks (GB)

(*) Notice: Subject to any disclaimer, the term of this patent is extended or adjusted under 35 U.S.C. 154(b) by 211 days.

(21) Appl. No.: 13/123,882

(22) PCT Filed: Oct. 14, 2009

(86) PCT No.: PCT/GB2009/051366
§ 371 (c)(1),
(2), (4) Date: Apr. 12, 2011

(87) PCT Pub. No.: WO2010/043896
PCT Pub. Date: Apr. 22, 2010

(65) Prior Publication Data
US 2011/0197660 A1    Aug. 18, 2011

(30) Foreign Application Priority Data
Oct. 16, 2008  (GB) .................................. 0818921.9

(51) Int. Cl.
*G01N 27/08* (2006.01)

(52) U.S. Cl.
USPC ......................... 73/53.01; 210/638; 436/146

(58) Field of Classification Search
USPC .............. 73/53.01, 61.41; 210/194, 196, 263, 210/600, 662, 746, 748.1, 758; 422/82.02; 436/145, 146
See application file for complete search history.

(56) References Cited

U.S. PATENT DOCUMENTS

| 4,496,470 | A | | 1/1985 | Kapiloff et al. |
| 5,057,229 | A | | 10/1991 | Schulenburg |
| 5,272,091 | A | * | 12/1993 | Egozy et al. .................. 436/146 |

(Continued)

FOREIGN PATENT DOCUMENTS

| DE | 3 830 623 | 5/1989 |
| EP | 0 498 888 | 8/1992 |

(Continued)

OTHER PUBLICATIONS

International Preliminary Report on Patentability and Written Opinion, dated Apr. 28, 2011, 7 pages.

(Continued)

*Primary Examiner* — Leonard Chang
*Assistant Examiner* — Natalie Huls
(74) *Attorney, Agent, or Firm* — Drinker Biddle & Reath LLP

(57) ABSTRACT

A method of determining the TOC of a purified water stream is disclosed comprising at least the steps of: passing a supply water stream through a water purification apparatus including an oxidizer to provide a purified water stream, and dispensing at least a portion of the purified water stream; stopping the dispense of the purified water stream and recirculating the purified water stream as a recirculating water stream through at least a portion of the water purification apparatus including the oxidizer to provide a re-oxidized water stream; and measuring the conductivity value of the re-oxidized water stream to determine the TOC of the purified water stream. In this way, a determination of the TOC of the purified water stream of can be provided without requiring a dedicated TOC monitor at the point of dispense of the purified water stream.

15 Claims, 3 Drawing Sheets

(56) References Cited

U.S. PATENT DOCUMENTS

| | | | |
|---|---|---|---|
| 5,282,889 A | 2/1994 | Franklin | |
| 5,518,608 A | 5/1996 | Chubachi | |
| 5,935,441 A * | 8/1999 | O'Neill et al. | 210/638 |
| 6,129,099 A | 10/2000 | Foster et al. | |
| 6,579,445 B2 * | 6/2003 | Nachtman et al. | 210/85 |
| 6,767,408 B2 | 7/2004 | Kenowski et al. | |
| 7,060,136 B1 | 6/2006 | Zeiher et al. | |
| 7,938,909 B2 * | 5/2011 | Mortimer et al. | 134/18 |
| 2003/0141258 A1 | 7/2003 | Hatch | |
| 2004/0112838 A1 | 6/2004 | Martin | |
| 2006/0241874 A1 | 10/2006 | Carter | |
| 2008/0034846 A1 | 2/2008 | Mortimer et al. | |
| 2009/0316119 A1 * | 12/2009 | Parekh et al. | 355/30 |
| 2011/0192429 A1 * | 8/2011 | Underwood et al. | 134/34 |

FOREIGN PATENT DOCUMENTS

| | | |
|---|---|---|
| EP | 0 581 157 A1 | 2/1994 |
| EP | 0 504 520 | 12/1995 |
| EP | 0 581 157 B1 | 6/1999 |
| WO | WO 96/01999 | 1/1996 |
| WO | WO 99/42824 | 8/1999 |
| WO | WO 02/38507 | 5/2002 |
| WO | WO2004/040389 | 5/2004 |

OTHER PUBLICATIONS

Notice of Written Opinion of the International Preliminary Report, Feb. 2007.

International Search Report, dated /Feb. 10, 2010.

* cited by examiner

METHOD OF TOC MONITORING

FIELD OF THE INVENTION

The present invention relates a method of monitoring the total organic carbon content (hereinafter "TOC") of water in and being dispensed from water purification apparatus and units, particularly but not exclusively for laboratory water.

BACKGROUND

Water purification apparatus and units for use in laboratories and healthcare facilities are well known. Generally, they involve the reduction and/or removal of contaminants and impurities to very low levels. They typically contain a variety of technologies that remove particles, colloids, bacteria, ionic species and organic substances and/or molecules.

The levels of such contaminants and impurities can be monitored in various ways, one being to measure the total organic carbon content ("TOC") as a measure of any remaining organic substances in the water. TOC limits for various purities or grades of water are prescribed by various national and international bodies, for example the US and European pharmacopoeias (USP/EP), the American Society for Testing and Materials (ASTM) and the Clinical Laboratory Standards Institute (CLSI).

Dedicated TOC monitors are well known in the art; see for example the monitor shown in WO99/42824A1. A TOC monitor can be located at or near the point of dispense of purified water from a water purification unit to directly confirm the TOC of the dispensed water to a user and/or service engineer. However, dedicated TOC monitors are expensive, and also require separate maintenance, adding to the CAPEX and OPEX of such water purification units. They also use some of the purified water.

EP 0 498 888 A1 describes a method of measuring the total amount of organic substances in ultra-pure water by applying ultraviolet rays to ultra-pure water whose specific resistance value has been set to a known constant. However, this arrangement requires treatment of the feed water to ensure that this value is achieved and does not attempt to measure TOC of the water being dispensed.

Alternatively, the difference in specific resistance values before and after the application of ultraviolet rays to a water stream is used to estimate the TOC of the water being dispensed.

SUMMARY OF THE INVENTION

It is an object of the present invention to provide a simpler and more cost-effective method of monitoring the TOC of the purified water from the dispense point of a water purification apparatus or unit.

Thus, according to one aspect of the present invention, there is provided a method of determining the TOC of a purified water stream, comprising at least the steps of:
  (a) passing a supply water stream through a water purification apparatus including an oxidiser to provide a purified water stream, and dispensing at least a portion of the purified water stream;
  (b) stopping the dispense of the purified water stream and recirculating the purified water stream as a recirculating water stream through at least a portion of the water purification apparatus including the oxidiser to provide a re-oxidised water stream; and
  (c) Measuring the conductivity value of the re-oxidised water stream to determine the TOC of the purified water stream.

In this way, a determination of the TOC of the purified water stream of step (a) can be provided without requiring a dedicated TOC monitor at the point of dispense of the purified water stream.

The supply water stream may comprise any source of water, generally being a potable water source, generally available to a user from a mains supply or other continuous or large supply which may have been at least prior partially purified. Commonly, such a water source is provided from a tap or other standard supply device, having a line or other connection with the water purification apparatus.

The water purification apparatus may comprise any number of devices, parts, components, lines, etc, including but not limited to one or more of the following: pumps, meters, sensors, oxidisers, de-ionisers, valves, drains, control units and mechanisms, taps, filters, membranes.

One common oxidiser involves the use of ultraviolet light, and the short wavelength ultraviolet treatment of water for decomposing organic compounds or substances in water is well known in the art. Generally, ultraviolet light is able to decompose many organic compounds and substances that are contained or are residues in generally available water, by oxidising them to form ionic or charged species. Apparatus and instruments for providing suitable ultraviolet light are well known in the art, and typically involve emitting ultraviolet light at one or more specific wavelengths, such as at 185 nanometers, in an area or space through which the water passes.

In many water purification units or apparatus, oxidisers are provided as a distinct component, typically a separable component such as a replaceable cartridge, having an ultraviolet emitter therein close to which the water stream passes from an inlet to an outlet. The purification of water in the present invention may involve one or more oxidisers, being in series, parallel or both.

Ionic species created by the or each oxidiser are generally removed from the water stream, to provide a purified water stream, by the use of one or more de-ionisers. Many types and forms of de-ionisers are known in the art, and include, but are not limited to, one or more of the following; (electro)deionisation apparatus or units, reverse osmosis (RO) units or apparatus, ion-exchangers, resins and zeolites. The action and operation of a de-ioniser is well known in the art, and they are not further described in detail herein.

A water purification apparatus or unit may comprise a plurality of de-ionisers, including one or more "pre-treatment" ion exchangers upstream of an oxidiser, as well as one or more ion-exchangers downstream of the oxidiser.

In general, a water purification apparatus or unit of the present invention at least comprises: a water inlet, a pump, an oxidiser, a de-ioniser such as an ion-exchanger, and a water outlet (for dispense of the purified water). Such water purification apparatus generally only provide up to 1000 liters of purified water per hour, such as up to 5 l/min.

Such water purification apparatus are generally 'stand alone' units, generally only requiring connection to nearby water and electricity supplies to be operable. Thus, they are generally independent and/or movable units operating in or at a specific location such as a laboratory. Preferably, at least the majority of the purification actions or processes occur within a housing. They are intended to provide a purified water stream only, such stream not being in combination with any other substance or compound.

The purified water stream provided by step (a) is created by the reduction and/or removal of any or one or more of the contaminants and impurities in the supply water stream. This can involve the reduction and/or removal of one or more of the following: particles, colloids, bacteria, micro-organisms, ionic species, organic substances.

In general, water purification apparatus and units are intended to provide a purified water stream having a conductivity of less than 1 μS/cm, preferably less than 0.1 μS/cm, and more preferably less than 0.067 μS/cm. This can be equated to a purified water stream having a resistivity of at least 1 MΩ-cm, preferably at least 10 MΩ-cm, more preferably at least 15 MΩ-cm. Additionally, purity specifications can be made for organic species to content levels of less than 500 ppb of total organic carbon (TOC), preferably less than 50 ppb; bacteria to levels less than 100 colony forming units (cfu) per milliliter, preferably less than 1 cfu/ml; and for dissolved oxygen and/or particles.

The skilled man is aware of the relationship between conductivity and resistivity, such that either one or both measurements can be made by a suitable measurer or meter. Thus, the term "conductivity value" as used herein relates to the measurement of the conductivity and/or resistivity of a water stream, either one or both of which may be used to provide a determination of TOC.

The skilled man is also aware that conductivity and/or resistivity measurements or values are temperature dependent. Commonly, a temperature of 25° C. is used as a standard temperature when discussing and comparing conductivity and/or resistivity measurements, such that the conductivity of "pure" water is considered to be 0.055 μS/cm and the resistivity is considered to be 18.2 MΩ-cm, at 25° C.

The dispense of at least a portion of the purified water stream can be provided through any form or type of outlet or outlets, optionally being coordinated or separate.

The water purification apparatus may have a dispense mode or other such form of operation, and a recirculation mode. Preferably, the point of dispense involves at least one valve, more preferably operable between a dispense position and a recirculating position. One or more valves may also provide control over the volume and/or rate of flow of the purified water stream at the point of dispense.

The dispense may involve the dispense of all of the purified water stream being provided by the water purification apparatus, such as whilst the water purification apparatus is in a dispense mode. Optionally, a portion of the purified water stream may be contemporaneously or simultaneously recirculated through at least a portion of the water purification apparatus whilst the remainder of the purified water stream is being dispensed.

The movement of water streams through a water purification apparatus is generally provided by the use of one of more pumps known in the art, and not further discussed in detail herein.

Stopping of the dispense of the purified water stream may be carried out by the operation (usually through a controller) of one or more parts or components of the water purification apparatus, generally operation of one or more valves at or near the dispense, such as a 2-way valve able to move between a dispense position and a recirculating position.

Recirculating a purified water stream through at least a portion of a water purification apparatus is well known in the art. Typically it is intended to maintain the highest purity for the water stream by its re-passage through one or more of the purification processes or technologies, and by its continual movement, thereby preventing stagnation and the opportunity for any remaining bacteria and/or micro organisms to adhere to a surface and grow.

Recirculating the purified water stream, and/or any supply water stream that has entered the water purification apparatus prior to the stopping of the dispense of the purified water stream and which is downstream of the point of recirculation, provides a recirculating water stream. This is able to pass through any portion of the water purification apparatus, generally including at least the same pump, the oxidiser and optionally one or more de-ionisers.

The first part of the recirculating water stream, comprising the purified water stream created but not dispensed, then re-passes through the same oxidiser and provides a re-oxidised water stream. The re-oxidised water stream may continued to be recirculated, and/or be provided to the point of dispense in a manner known in the art.

Step (c) of the present invention comprises measuring a conductivity value, as defined hereinabove, of the re-oxidised water stream to determine the TOC of the purified water stream.

The determination of the TOC of a water stream based on the change in conductivity value on passage through an oxidiser is well known in the art, and generally comprises measuring the conductivity and/or a related value of the water stream before and after the oxidiser and then using the change in conductivity to calculate the TOC in the water stream prior to the oxidiser.

The relationship between TOC and the conductivity generated is a function of the oxidising device's properties, its housing's geometry, the rate of flow and the concentration and the nature of the species in the water stream entering the oxidiser. The change in conductivity will also be a function of the conductivity of the water stream entering the oxidiser. These effects can be determined experimentally for the actual components being used, and a calibration can be produced to provide a known or expected level of oxidation of organic substances during standard and/or normal operation of the oxidiser.

Typically, this provides a known or expected level of oxidation between 50 and 100%, such as 70% or 80%. The efficiency of an oxidiser may be estimated by periodically increasing the time the recirculated water stream spends in the oxidiser sufficiently to ensure complete oxidation of the or any organic substances present. The relationship between the change in conductivity during normal operation and the change in conductivity during complete oxidation can be used to check the efficiency of the oxidation and the values being used in the algorithms, and modify these values or alert the user such as raising an alarm, as necessary.

The TOC in the water stream prior to the oxidiser can be provided or determined or otherwise sufficiently estimated in a number of ways, and the invention is not limited thereto. These include measuring the conductivity value of the recirculating stream before the oxidiser, measuring the conductivity of the purified water stream dispensed, usually by a simple line cell, and/or assuming a conductivity value based on known or expected provision of the purified water stream and/or operation of the water purification apparatus, such as 0.055 μS/cm.

By knowing the conductivity of the recirculating water stream and with knowledge of the efficiency of the oxidiser, it is possible to determine the TOC of the purified water stream following its recirculation as at least the first part of a recirculating water stream through the oxidiser. Thus, using a change in conductivity value on passage through the oxidiser of, by way of example only, 0.15 μS/cm, equivalent to the oxidation of 3.2 ppb TOC, and using an efficiency for an ultraviolet light emitter of 80%, allows the determination of the TOC in the recirculating water stream, and hence the purified water stream prior to stopping the dispense, of 4.0 ppb.

Apparatus and devices for measuring a conductivity value of a water stream are known in the art, and include in-line conductivity cells. One or more such apparatus or devices may already be a part or component of the water purification apparatus, such that they could be used for measuring the conductivity value of the re-oxidised stream, as well as conductivity values of the supply and immediate water streams and for the recirculating water stream.

In one embodiment of the present invention, the movement and/or flow of the recirculating water stream through the portion of the water purification apparatus including the oxidiser may be varied, including delayed, such as slowed and/or stopped, for one or more intervals. In this way, a recirculating water stream could be stopped or held in the oxidiser, to increase the extent of oxidation and hence increase the accuracy of the TOC determination based on the subsequent conductivity value measurement.

BRIEF DESCRIPTION OF THE DRAWINGS

For the purpose of the illustrating the invention, an embodiment of the present invention will now be described by way of example only, and with reference to the accompanying drawings.

DESCRIPTION OF THE PREFERRED EMBODIMENTS

Figure 1:
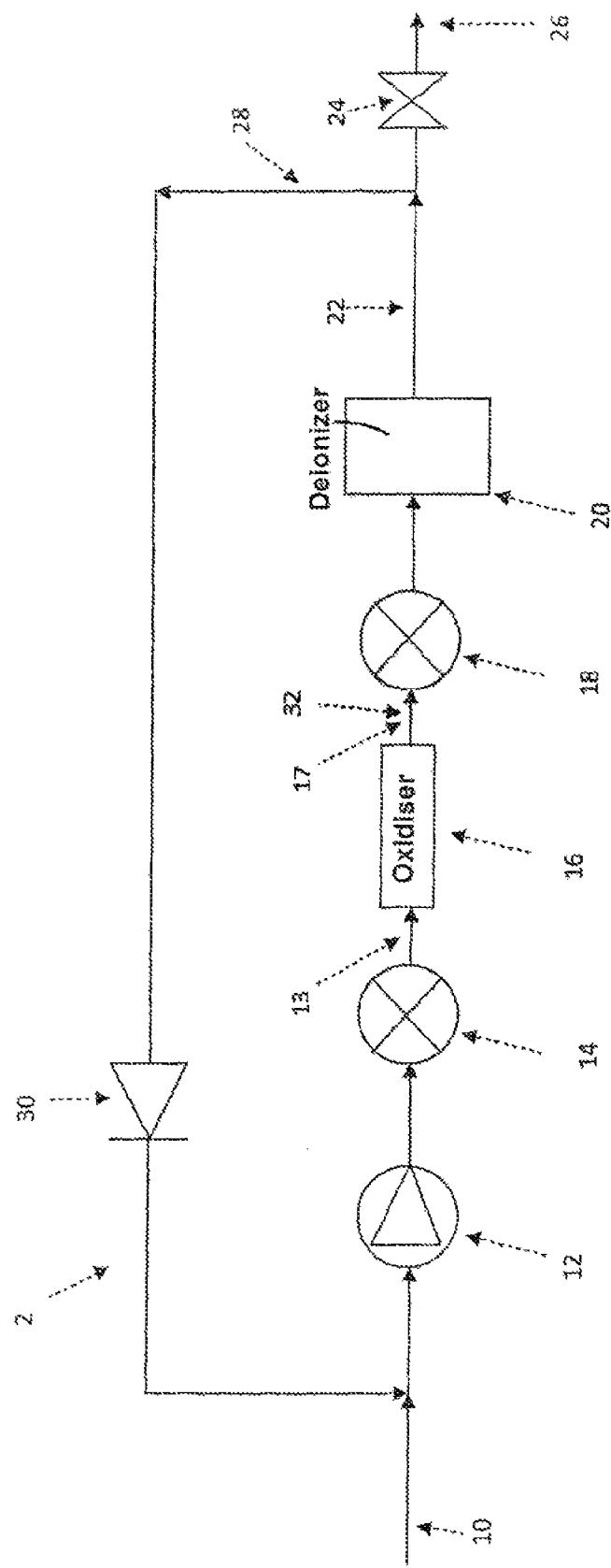
FIG. 1 schematically shows a method of determining the TOC of a purified water stream according to one embodiment of the present invention.

Referring to the drawing, FIG. 1 shows a method of determining the TOC of the purified water stream. Additional parts and/or components of the water purification apparatus are not shown in FIG. 1 for clarity purposes.

In FIG. 1, there is provided a supply water stream 10 from a water source (not shown), which may have been pre-treated by one or more steps and/or processes in a manner known in the art, such as one or more filters or membranes or de-ionisers to reduce impurities.

The supply water stream 10 passes through a pump 12 being part of a water purification apparatus 2. After the pump 12, the supply water stream 10 passes through a first line cell 14, in which a conductivity value of the supply water stream 10 can be taken if desired, followed by passage into an oxidiser 16 comprising one or more ultraviolet light emitters. The oxidiser 16 oxidises a calibrated percentage of any organic compounds or substances in the supply water stream 10 to create ionised species in a manner known in the art. The post-oxidiser water stream 17 passes through a second line cell 18, being the same or similar to that of the first line cell 14, in which a second conductivity value can be taken. Thereafter, the post-oxidiser stream 17 passes through one or more de-ionisers such as a deionisation unit 20 comprising one or more ion exchangers, to provide a purified water stream 22.

The purified water stream 22 can be provided through a valve 24 as a dispensed stream 26 to a point of dispense and/or to be otherwise dispensed to a user. It is the purity of this purified water stream 22 which is of particular importance to the user. Once the user is provided with the required purified water stream dispense, the valve 24 can be operated (by a controller not shown) to move between a dispense position and re-circulating position, such that remaining purified water stream 22 prior to the valve 24 is directed to a recirculation line or loop 28, and thus provided as a recirculating water stream 28 (the same reference number being assigned to the line and the stream in said line). At the same time the supply line 10 may be reduced, preferably closed.

The recirculating water stream 28 passes through a one-way valve 30 and then back into the water purification apparatus 2, especially through the pump 12, the first line cell 14 and the oxidiser 16, to provide a re-oxidised water stream (now labelled 32).

It is now possible for the first line cell 14 and the second line cell 18 to measure the conductivity values of the recirculating stream 28 and re-oxidised water stream 32 respectively. As the recirculating stream 28 and the re-oxidised water stream 32 are provided from a portion of the purified water stream 22 having been re-circulated through the re-circulation loop 28, a determination of the TOC of the purified water stream 22 can be made from the conductivity values of the recirculating water stream 28 and the re-oxidised water stream 32 based on the known or measured efficiency of the oxidiser 16.

When the valve 24 is moved between its dispense position and its recirculation position, the pump 12 recirculates water within the water purification apparatus without taking water from the supply stream 10, such that the measurement of the conductivity value by the second line cell 18 is only of a re-oxidised water stream 32 wholly provided by the recirculating water stream 28, rather than any portion of supply water stream 10.

Optionally, once the oxidiser 16 is supplied with the recirculating water stream 28, the pump 16 may be temporarily slowed or stopped, such that the portion of the recirculating water stream 28 in the oxidiser 16 may have an increased delay or period, such as 2-5 minutes, to increase the oxidising action of the oxidiser 16, and so provide a more highly oxidised water stream, This increases the sensitivity of measurements made by at least the second line cell 18.

It will be appreciated that although specific embodiments of the invention have been described herein for the purposes of illustration, various modifications may be made without deviating from the spirit of the scope of the invention.

It will also be appreciated that the present invention can advantageously be used in conjunction with a means of estimating the TOC in the purified water stream from a conventional water purification apparatus. For example, and referring to FIG. 1, while the water purification apparatus 2 is dispensing a purified water stream 22, by measuring the difference in conductivity values between the supply stream 10 (measurable by the first line cell 14) and the post-oxidiser water stream 17 produced by the oxidiser 16 (measurable by the second line cell 18), and knowing the efficiency of oxidiser 16, it is possible to determine the TOC of the supply stream 10 and the concentration of the oxidised species (as TOC) in the water stream 17.

The ions and charged species which produce the increased conductivity in the post-oxidiser water stream 17 are removed subsequently by the deioniser 20. The TOC in the purified water stream 22 can therefore be estimated as the residual TOC remaining after the oxidised species are removed by the deioniser 20, (assuming the deioniser 20 makes a negligible contribution of additional TOC or making allowance for any such contribution).

This approach has the benefit of a very rapid response. For example, as the measurements are made virtually instantaneously, and as the water can subsequently be passed through a known volume, for example 1 liter, taking a known time, for example 30 seconds, the estimated TOC value can be displayed as the purified water stream 22 is being dispensed. However, it is not a direct TOC measurement carried out on purified water stream 22.

The present invention has a slower response, but is a direct measure of the TOC of the purified water stream 22. The two approaches may be used to complement each other. A comparison of the results by the two approaches may also be used to calibrate and/or increase the accuracy of the more rapid estimation of TOC and monitor the potential release of TOC from the deioniser 20.

In particular, the present invention is able to 're-use' one or more of the line cells and the oxidiser used in the water purification process of the supply water stream, to determine the TOC in the purified water stream without requiring a separate TOC meter at or near the point of dispense.

Figure 2:
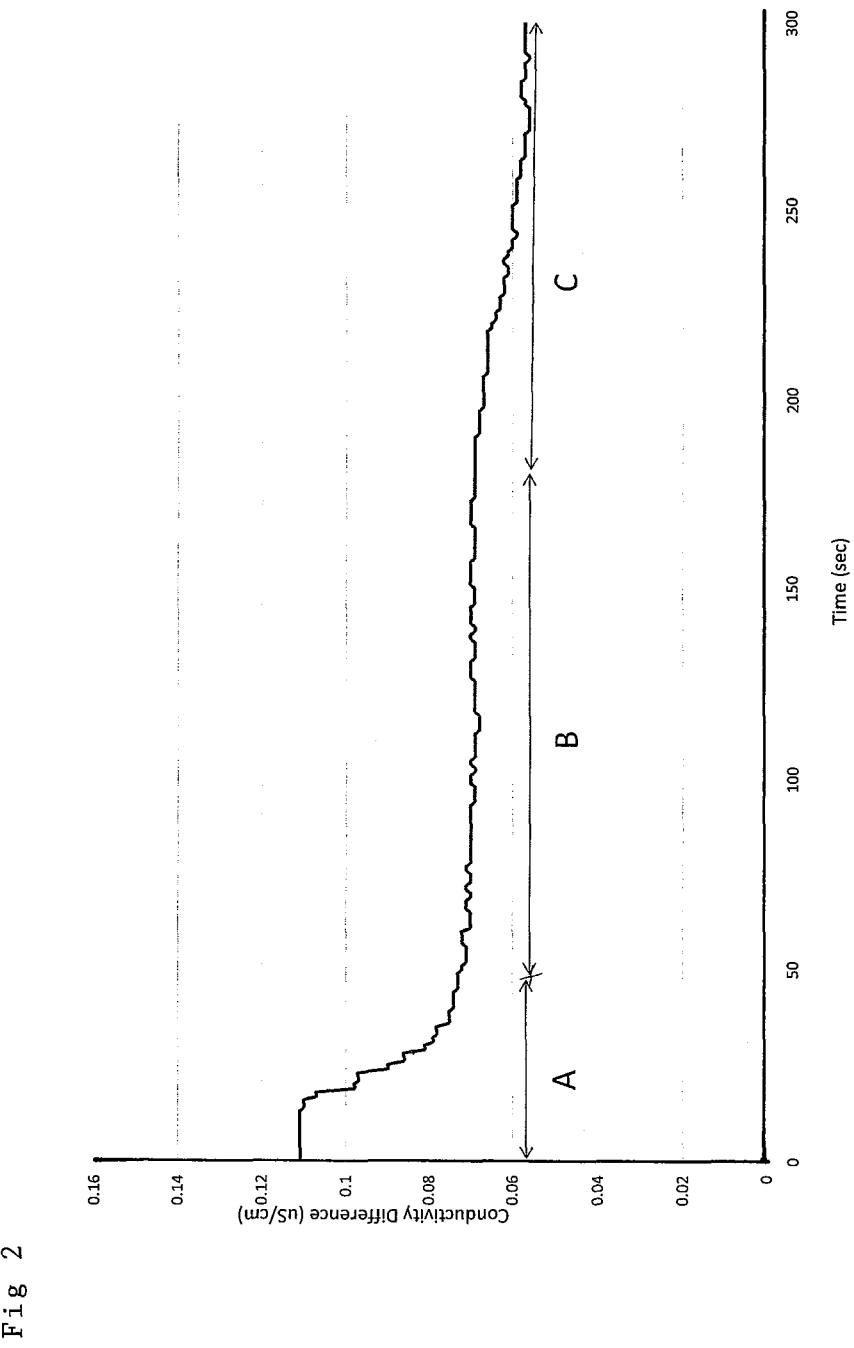
FIG. 2 is a graph of the conductivity difference over time across a UV housing after stopping a water dispense, running at 1.2 l/min.
Figure 3:
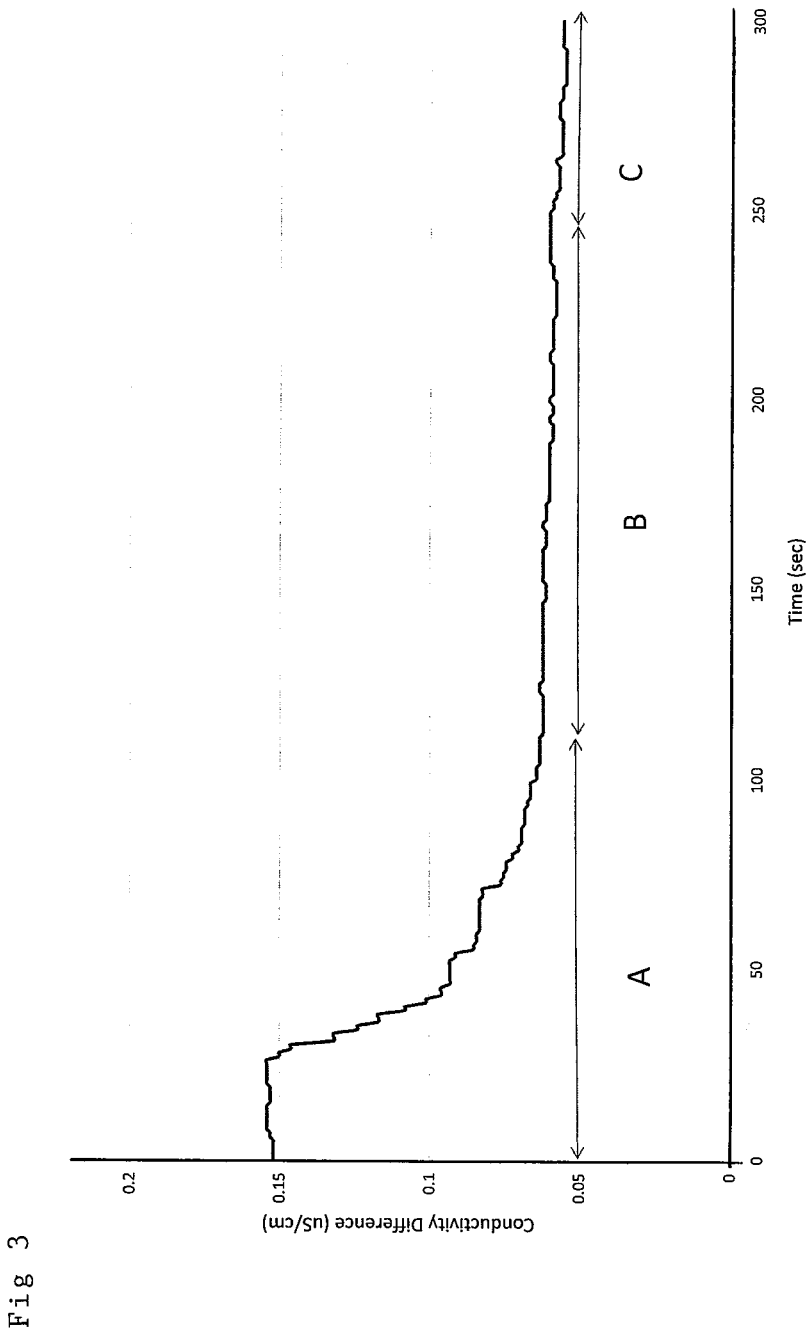
FIG. 3 is a graph of the conductivity difference over time across a UV housing after stopping a water dispense, running at 0.5 l/min.

Examples of the present invention will now be described with reference to the graphs in the accompanying FIGS. 2 and 3 which show:

FIG. 2 is a graph of the conductivity difference over time across a UV housing after stopping a water dispense, running at 1.2 l/min; and FIG. 3 is a graph of the conductivity difference over time across a UV housing after stopping a water dispense, running at 0.5 l/min.

Example 1

Using the water purification apparatus described hereinabove in relation to FIG. 1, a first example comprises providing a supply feedwater stream with a TOC of 12 ppb through the line 10, and dispensing water at a rate of 1.2 l/min as a dispensed stream 26. During this time, conductivity readings of the water passing through the first and second line cells 14 and 18 are logged. The difference in conductivity readings between these line cells 14 and 18 is about 0.11 $\mu$S/cm as shown at the start (section A) of the graph of FIG. 2.

By calibration at this flow rate, this corresponds to a feedwater TOC of 12 ppb. This TOC is then reduced as the water stream passes through the oxidiser (being a UV chamber for Example 1) 16 and the deionisation unit 20 to give a final TOC in the purified water stream 22 and as the dispensed stream 26 of 7 ppb.

When the dispense is stopped by closing the valve 24, the purified water stream 22 now recirculates along the recirculation line 28 and back through the pump 12, the first line cell 14, the oxidiser 16, and the second line cell 18.

This initial recirculating water stream acts as a new feed to the first line cell 14, the oxidiser 16, and the second line cell 18. As this new feed of water has a lower TOC, the difference in conductivity between the first line cell 14 and the second line cell 18 is lower—as indicated in section B in FIG. 2. This difference is now only 0.065 $\mu$S/cm, and it corresponds with the calibration of 7 ppb TOC.

This initial recirculating water stream is the same water that would have been dispensed (as dispensed steam 26) had the dispense continued. Therefore, the conductivity difference at section B of FIG. 2 gives a direct estimation of the TOC of the dispensed water 26. Thus, the existing first and second line cells 14, 18 have been able to determine the TOC in the purified water stream 26 without requiring a separate TOC meter at or near the point of dispense 26.

As the water continues to recirculated after the initial period, it will continue to be purified and the TOC will drop further as shown in section C of FIG. 2.

Example 2

Using the water purification apparatus described hereinabove in relation to FIG. 1, a second example comprises providing a supply feedwater stream with a TOC of 12 ppb through the line 10, and dispensing water at a rate of 0.5 l/min as a dispensed stream 26. During this time, conductivity readings of the water passing through the first and second line cells 14 and 18 are logged. The difference in conductivity readings between these line cells 14 and 18 is about 0.15 $\mu$S/cm as shown at the start (section A) of the graph of FIG. 3.

By calibration at this flow rate, this corresponds to a feedwater TOC of 12 ppb. This TOC is then reduced as the water stream passes through the oxidiser (being a UV chamber for Example 2) 16 and the deionisation unit 20 to give a final TOC in the purified water stream 22 and as the dispensed stream 26 of 5 ppb.

When the dispense is stopped by closing the valve 24, the purified water stream 22 now recirculates along the recirculation line 28 and back through the pump 12, the first line cell 14, the oxidiser 16, and the second line cell 18.

This initial recirculating water stream acts as a new feed stream to the first line cell 14, the oxidiser 16, and the second line cell 18. As this new feed of water has a lower TOC, the difference in conductivity between the first line cell 14 and the second line cell 18 is lower—as indicated in section B in FIG. 3. This difference is now only 0.06 $\mu$S/cm, and it corresponds with the calibration of 5 ppb TOC.

This initial recirculating water stream is the same water that would have been dispensed (as dispensed steam 26) had the dispense continued. Therefore, the conductivity difference at section B of FIG. 3 gives a direct estimation of the TOC of the dispensed water 26. Thus, the existing first and second line cells 14, 18 have been able to determine the TOC in the purified water stream 26 without requiring a separate TOC meter at or near the point of dispense 26.

As the water continues to recirculated after the initial period, it will continue to be purified and the TOC will drop further as shown in section C of FIG. 3.

The lengths of the time periods of sections A and B in Example 2 and FIG. 3 are longer than those in Example 1 and FIG. 2 due to the lower flow rate; this also increases both the conductivity differences and the TOC reduction in Example 2.

The invention claimed is:

1. A method of determining the total organic carbon (TOC) of a purified water stream, comprising at least the steps of:
   (a) passing a supply water stream through a water purification apparatus including an oxidiser and one or more ion-exchangers downstream of the oxidiser, to provide a purified water stream, and dispensing at least a portion of the purified water stream through a valve at a point of dispense as a dispensed stream;
   (b) stopping the dispense of the purified water stream by operating the valve to move between a dispense position and a recirculating position and recirculating the purified water stream as a recirculating water stream through at least a portion of the water purification apparatus including the oxidiser to provide a re-oxidised water stream;

(c) measuring a conductivity value of the recirculating water stream prior to the oxidiser at a first location in the water purification apparatus that is prior to any ion-exchangers so as to provide a conductivity measurement of the recirculating water stream;

(d) channeling the recirculating water stream from the first location to the oxidiser without passing through any ion-exchangers;

(e) measuring a conductivity value of the re-oxidised water stream at a second location downstream from the oxidiser and prior to the re-oxidised water stream passing through any ion-exchangers; and (f) using the measurements to determine the TOC of the purified water stream of step (a) at the point of dispense of the purified water stream.

2. A method as claimed in claim 1 wherein the water purification apparatus at least comprises: a water inlet, a pump, an oxidiser, a de-ioniser, and a water outlet.

3. A method as claimed in claim 2 wherein the oxidiser comprises one or more ultraviolet light emitters.

4. A method as claimed in claim 2 wherein the recirculating water stream is delayed in the oxidiser in step (b).

5. A method as claimed in claim 2 further comprising measuring the conductivity value of the purified water stream dispensed and/or assuming a conductivity value for the recirculating water stream prior to the oxidiser, and using said value in determining the TOC of the purified water stream.

6. A method as claimed in claim 2 to calibrate and/or increase the accuracy of the estimation of TOC in the purified water stream during a dispense, the estimate of the TOC being determined from the measurement of the difference in conductivity values between the supply stream and the post oxidiser water stream during the dispense.

7. A method as claimed in claim 1 wherein the oxidiser comprises one or more ultraviolet light emitters.

8. A method as claimed in claim 7 wherein the recirculating water stream is delayed in the oxidiser in step (b).

9. A method as claimed in claim 7 further comprising measuring the conductivity value of the purified water stream dispensed and/or assuming a conductivity value for the recirculating water stream prior to the oxidiser, and using said value in determining the TOC of the purified water stream.

10. A method as claimed in claim 7 to calibrate and/or increase the accuracy of the estimation of TOC in the purified water stream during a dispense, the estimate of the TOO being determined from the measurement of the difference in conductivity values between the supply stream and the post oxidiser water stream during the dispense.

11. A method as claimed in claim 1 wherein the recirculating water stream is delayed in the oxidiser in step (b).

12. A method as claimed in claim 11 further comprising measuring the conductivity value of the purified water stream dispensed and/or assuming a conductivity value for the recirculating water stream prior to the oxidiser, and using said value in determining the TOC of the purified water stream.

13. A method as claimed in claim 11 to calibrate and/or increase the accuracy of the estimation of TOC in the purified water stream during a dispense, the estimate of the TOC being determined from the measurement of the difference in conductivity values between the supply stream and the post oxidiser water stream during the dispense.

14. A method as claimed in claim 1 further comprising measuring the conductivity value of the purified water stream dispensed and/or assuming a conductivity value for the recirculating water stream prior to the oxidiser, and using said value in determining the TOC of the purified water stream.

15. A method as claimed in claim 1 to calibrate and/or increase the accuracy of the estimation of TOC in the purified water stream during a dispense, the estimate of the TOC being determined from the measurement of the difference in conductivity values between the supply stream and the post oxidiser water stream during the dispense.

* * * * *